(12) United States Patent
Ghodbane et al.

(10) Patent No.: US 12,415,015 B2
(45) Date of Patent: Sep. 16, 2025

(54) KIT FOR COMPOSITION FOR TISSUE TRACT SEALING

(71) Applicant: Ethicon, Inc., Raritan, NJ (US)

(72) Inventors: Salim Ghodbane, Piscataway, NJ (US); Ashley DeAnglis, Skillman, NJ (US); Sridevi N. Dhanaraj, Somerville, NJ (US); Guanghui Zhang, Belle Mead, NJ (US)

(73) Assignee: Ethicon, Inc., Raritan, NJ (US)

( * ) Notice: Subject to any disclaimer, the term of this patent is extended or adjusted under 35 U.S.C. 154(b) by 564 days.

(21) Appl. No.: 17/932,682

(22) Filed: Sep. 16, 2022

(65) Prior Publication Data

US 2023/0085152 A1    Mar. 16, 2023

Related U.S. Application Data

(60) Provisional application No. 63/245,178, filed on Sep. 16, 2021.

(51) Int. Cl.
*A61L 24/00* (2006.01)
*A61L 24/10* (2006.01)

(52) U.S. Cl.
CPC ......... *A61L 24/0031* (2013.01); *A61L 24/001* (2013.01); *A61L 24/0036* (2013.01); *A61L 24/0042* (2013.01); *A61L 24/104* (2013.01); *A61L 24/106* (2013.01); *A61L 24/108* (2013.01); *A61L 2400/04* (2013.01); *A61L 2400/06* (2013.01)

(58) Field of Classification Search
CPC .. A61L 24/0031; A61L 24/106; A61L 24/108; A61L 24/001; A61L 24/0036; A61L 24/0042; A61L 24/104; A61L 2400/04; A61L 2400/06
See application file for complete search history.

(56) References Cited

U.S. PATENT DOCUMENTS

| | | |
|---|---|---|
| 6,045,570 A | 4/2000 | Epstein et al. |
| 6,121,232 A | 9/2000 | Nur et al. |
| 7,125,569 B2 | 10/2006 | Nur et al. |

FOREIGN PATENT DOCUMENTS

| | | | |
|---|---|---|---|
| CN | 110743038 B | 9/2021 | |
| WO | WO-9222312 A1 * | 12/1992 | ........... A61K 38/363 |
| WO | 9833533 A1 | 8/1998 | |
| WO | 02095019 A1 | 11/2002 | |
| WO | 03007845 A1 | 1/2003 | |
| WO | 2008016983 A2 | 2/2008 | |
| WO | 2014202760 A2 | 12/2014 | |
| WO | 2023042146 A1 | 3/2023 | |

OTHER PUBLICATIONS

Yousem et al., "Pulmonary Pathologic Alterations Associated with Biopsy Inserted Hydrogel Plugs", Human Pathology, vol. 89, Apr. 20, 2019, pp. 4-43.
International Search Report and Written Opinion received for Application No. PCT/IB2022/058770, mailed on Dec. 16, 2022, 15 pages.

* cited by examiner

*Primary Examiner* — Patrick D Niland
(74) *Attorney, Agent, or Firm* — David R. Crichton; Leo B. Kriksunov

(57) ABSTRACT

The present invention provides a kit for preparing a composition for sealing a lung tract, comprising: (a) a first component comprising: (i) a fibrinogen solution, and (ii) prewet gelatin particles in an aqueous solution; and (b) a second component comprising: (i) a thrombin solution, and (ii) a dry gelatin powder; wherein the first and second components are stored separately and configured for mixing together to form a composition that is flowable and crosslinkable. The composition may be used to seal tissue tracts such as lung tissue tracts.

7 Claims, 5 Drawing Sheets

Step 1

Step 2

Step 3

Step 4

Step 1

Step 2

Step 3

Step 4

KIT FOR COMPOSITION FOR TISSUE TRACT SEALING

FIELD OF THE INVENTION

The present invention provides a kit for preparing a composition for sealing a lung tract, comprising: (a) a first component comprising: (i) a fibrinogen solution, and (ii) prewet gelatin particles in an aqueous solution; and (b) a second component comprising: (i) a thrombin solution, and (ii) dry gelatin particles; wherein the first and second components are stored separately and configured for mixing together to form a composition that is flowable and cross-linkable, along with methods of using the composition for closing punctures in tissue such as those created by lung biopsies.

BACKGROUND OF THE INVENTION

Image-guided percutaneous transthoracic needle biopsy ("PTNB") is an established procedure for patients with suspected pathologic processes, such as bronchogenic carcinoma. The goal of the procedure is to obtain tissue for cytologic or histologic examination. The procedure is typically performed with image guidance by a radiologist. Imaging modalities utilized include fluoroscopy, computed tomography (CT), and ultrasound.

PTNB is classified according to the type of needle. Fine needle aspiration biopsy is performed to provide cytological specimens and larger diameter cutting needles produce histological specimens. Historically, cutting needles have been associated with a relatively high incidence of complications, but with the introduction of automated cutting needles comparable rates between fine needle aspiration and cutting needles have been demonstrated.

During PTNB, an aspiration (18-22 gauge) or cutting needle (14-20 gauge) is placed under image guidance for sample recovery. A coaxial technique may be used to allow for multiple passes within the lung tract and to reduce the number of pleural punctures. In this technique, a thin-walled introducer needle (13-19 gauge) is first inserted, localized to the lesion, and subsequently the aspiration or cutting needle is inserted.

Although the procedure is considered safe and effective, the incidence of pneumothorax is still significant, ranging from 12 to 61%, with 2 to 15% requiring a chest drain. The risk of pneumothorax increases significantly if the lesion is not adjacent to the pleura. Most complications occur immediately or within the first hour following the biopsy. Therefore, following the procedure, the patient is placed in a puncture-site-down position and remains under supervision for at least one hour.

As an alternative to PTNB, transbronchial needle aspiration ("TBNA") is a minimally invasive technique allowing for the sampling of mediastinal nodes. When integrated with endobronchial ultrasonography ("EBUS"), accurate definition of mediastinal structures is possible. Modern devices integrate an ultrasonic bronchoscope into the needle allowing for real time visualization of the area of interest. The diagnostic yield of EBUS-TBNA in lung cancer screening has been reported to have a sensitivity as high as 95.7%. As a result, EBUS-TBNA is becoming widely adopted as the standard of care for sampling mediastinal lymph nodes.

EBUS-TBNA devices include an ultrasound linear processing array and a retractable needle. EBUS-TBNA was originally performed with a dedicated 22-gauge aspiration needle; however, larger 21-gauge needles were introduced more recently. EBUS-TBNA are carried out in the proximal lumen of level 9 bronchi, as they are restricted by the outer diameter of the bronchoscope (6.9 mm).

Although complications are very low in EBUS-TBNA, incidence of pneumothorax is still significant. The rate of pneumothorax has been estimated to be from 0.53% to 16.7% following EBUS-TBNA. Moreover, PTNB and EBUS-TBNA procedures result in relatively large, cylindrical lesions along the order of 28 mm in diameter and 5 cm in length.

Patients in which enlarging pneumothoraxes are observed must be treated with the placement of a chest tube. However, there is no universally accepted approach to reduce pneumothorax rate. Multiple solutions have been employed, including the rapid roll over and deep expiration and breath-hold technique, but these techniques have only shown mild/moderate effects, with a risk reduction of 0.1-15.7%.

Others have investigated the instillation of various sealant materials into the lesion, including autologous blood clot, fibrin glue, and gelatinous foam, but none have achieved widespread use in daily practice. These methods have also suffered from variable results, possibly a result of operator-dependence, manufacturing differences and variations in practice. Autologous blood clot has demonstrated moderate efficacy but suffers from long preparation times in the operating room. Although fibrin glue and gelatin techniques have demonstrated some promising results in published data, they have not been studied extensively.

More recently, a synthetic polyethylene glycol plug has been commercialized as part of the BIOSENTRY Tract Sealant System (AngioDynamics, Inc.). In a randomized, multicenter clinical trial, the BIOSENTRY system resulted in the absence of pneumothorax in 85% of patients which was statistically greater than the control group (69%). However, as reported by Yousem, S. A., et al., *Pulmonary pathologic alterations associated with biopsy inserted hydrogel plugs*. Hum Pathol, 2019. 89: p. 40-43, the solid nature of the BIOSENTRY plug induces only a foreign body giant cell reaction and an encapsulation of the hydrogel by 21 days. Accordingly, a more porous plug would lead to a reduced foreign body reaction and more rapid healing.

WO 2008/016983 relates to wound sealing compositions comprising first and second cross-linkable components and at least one hydrogel-forming component. The compositions may also include rapidly acting materials, for example a tissue sealant, and the compositions exhibit minimal swelling properties. The first and second cross-linkable components may each, for example, be polyethylene glycols, and the hydrogel-forming component may, for example, be gelatin that may comprise subunits having sizes ranging from about 0.01 mm to about 5 mm when fully hydrated and have an equilibrium swell ranging from about 400% to about 5000%. The first and second components react under in-vivo conditions to form a cross-linked matrix, while the hydrogel-forming component rapidly absorbs the biological fluid coming through the tissue breach, as well as strengthens the resultant physical sealant matrix barrier formed as the first and second components cross-link.

SURGIFOAM® Absorbable Gelatin Sponges, commercially available from Ethicon Inc., Somerville, NJ, are cross-linked, gelatin-based hemostats in dry, solid, sponge form. SURGIFOAM® Absorbable Sponges are sterile, porcine, absorbable gelatin sponges capable of liquefying within 2 to 5 days when applied to bleeding mucosal regions and are completely absorbed within 4 to 6 weeks. SURGIFOAM® sponges are available in two shapes, cube or flat. Although gelatin is known to absorb 40 times its weight in blood and swell to up to 200% of its initial volume in vivo, this swelling is relatively slow and results in a low swelling pressure. Accordingly, SURGIFOAM® labeling advices, "[w]hen placed into cavities or closed tissue spaces, minimal preliminary compression is advised, and care should be exercised to avoid overpacking (the sponge expands upon absorption of liquid). SURGIFOAM® Sponge may swell to its original size on absorbing fluids, creating the potential for nerve damage."

SURGIFOAM® powder is a dry powder made by milling the SURGIFOAM sponges and sieving through openings less than 3 mm.

SURGIFLO® Hemostatic Matrix, also commercially available from Ethicon Inc. is a kit for producing a hemostatic gelatin paste, which is prepared by mixing gelatin with saline and subsequent transferring a gelatin matrix-saline solution mixture back and forth between two connected syringes several times. The gelatin particles in SURGIFLO® have a higher degree of cross-linking than the SURGIFOAM® powder.

FLOSEAL® Hemostatic Matrix, commercially available from Baxter is likewise a kit for producing a hemostatic gelatin paste. Once a substantially homogenous paste composition is achieved, the hemostatic pastes can be applied to a bleeding site by extruding the pastes from the syringe to promote hemostasis.

Applicants have now discovered that an improved composition for control of pneumostasis and hemostasis even in larger tracts such as those resulting from PTNB or EBUS-TBNA procedures may be made by combining: (a) a first component comprising: (i) a fibrinogen solution, and (ii) prewet gelatin particles in an aqueous solution; with (b) a second component comprising: (i) a thrombin solution, and (ii) dry gelatin particles. The first and second components are stored separately, for example in a kit, and configured for mixing together at the point of use to form a composition that is flowable and readily cross-linkable for example at 37° C. The composition may be inserted into a tissue tract for efficient and fast closure thereof.

SUMMARY OF THE INVENTION

The present invention provides a kit for preparing a composition for sealing a lung tract, comprising: (a) a first component comprising: (i) a fibrinogen solution, and (ii) prewet gelatin particles in an aqueous solution; and (b) a second component comprising: (i) a thrombin solution, and (ii) dry gelatin particles; wherein the first and second components are stored separately and configured for mixing together to form a composition that is flowable and cross-linkable.

The present invention also provides a method of sealing a lung tract, comprising mixing (a) a first component comprising: (i) a fibrinogen solution, and (ii) prewet gelatin particles in an aqueous solution; and (b) a second component comprising: (i) a thrombin solution, and (ii) dry gelatin particles to form a flowable, rapidly cross-linkable composition at 37° C.; and injecting the composition into a lung tract.

DETAILED DESCRIPTION OF THE INVENTION

Figure 1:
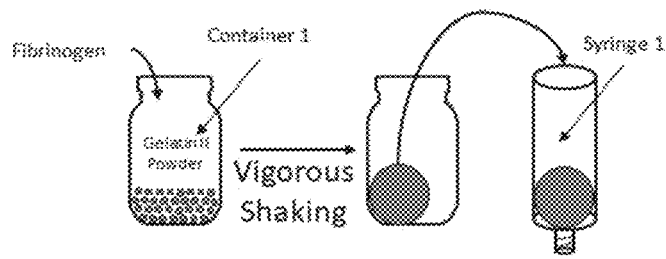
FIG. 1 is a diagram of the process used to make the comparative kit of Example 1.
Figure 1:
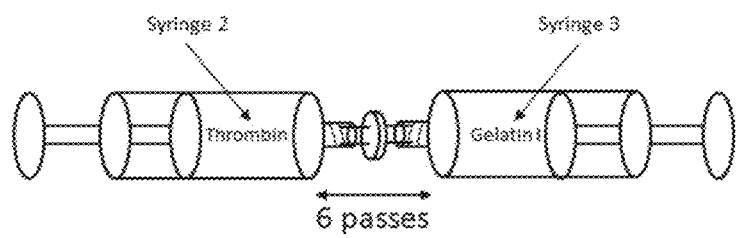
Figure 1:
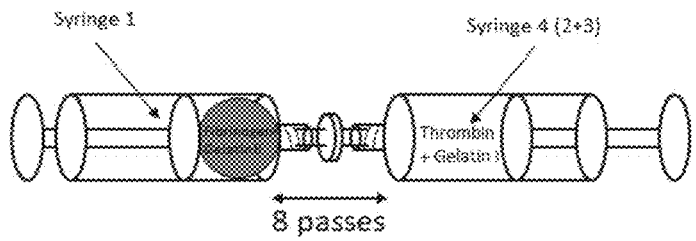
Figure 1:
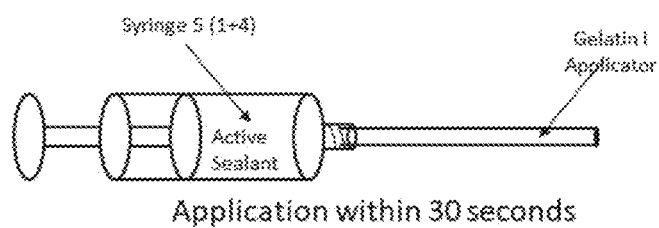

As used herein, "foam" means a solid, porous material having pores open to the surface of the material.

As used herein, "biocompatible" means compatible with living tissue or a living system by not being toxic, injurious, or physiologically reactive therewith and not causing immunological rejection thereby.

As used herein, "biologically absorbable" or "resorbable" means capable of degradation in the body to smaller molecules having a size that allows them to be transported into the blood stream. Such degradation and transportation gradually remove the material referred to from the site of application. For example, gelatin can be degraded by proteolytic tissue enzymes to absorbable smaller molecules, whereby the gelatin, when applied to tissue, typically is absorbed within about 4-6 weeks, and when applied to bleeding surfaces or mucous membranes, typically liquefies within 2 to 5 days.

As used herein, "hemostasis" means the process by which bleeding diminishes or stops. During hemostasis three steps occur in a rapid sequence. Vascular spasm is the first response as the blood vessels constrict to allow less blood to be lost. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue." Accordingly, a hemostatic material or compound is capable of stimulating hemostasis.

As used herein, "pneumostasis" means to deliver a material(s) to pulmonary tissue to close or seal one or more air leaks.

Unless otherwise indicated, percentages and amounts refer to percentages or amounts by weight, and ratios are weight ratios. Unless stated otherwise, all ranges are inclusive of the endpoints, e.g., "from 4 to 9" includes the endpoints 4 and 9.

Gelatin Particles

Both the prewet gelatin particles and the dry gelatin particles are made from absorbable gelatin sponges that meet the specifications defined by the United States Pharmacopeia (e.g., USP 29). The porous structure and the degree of cross-linking of the sponges are measured by water absorption and by digestibility following the USP methods. For each type of particles, the sponge should absorb not less than 35 times its weight of water, and the average digestion time by pepsin is not more than 75 minutes.

The prewet gelatin particles are made by mechanically milling the sponges into fine particles, and mixing the particles with an aqueous solution, for example saline solution. They may have a particle size D90 of less than 1000 microns. That is, 90% of the prewet gelatin particles may have a diameter less than 1000 microns. The degree of cross-linking in the prewet gelatin particles is such that they have a digestion time of more than 30 minutes, but not more than 75 minutes measured by the USP digestibility test (for e.g. as referenced in USP 34 monograph). The prewet gelatin particles have a higher degree of cross-linking degree than dry gelatin particles The dry gelatin particles are made by milling the gelatin sponges. They may have a particles size D90 of less than 2000 microns. That is, 90% of the dry gelatin particles may have a diameter less than 2000 microns. The degree of cross-linking in the dry gelatin particles is such that they have a digestion time of less than 30 minutes measured by the USP digestibility test. The dry gelatin particles when mixed with aqueous solution have a higher degree of swelling (absorbing liquid at least 35 times its own dry weight as described in USP 34 monograph) than the prewet gelatin particles.

First Component

The kit of the invention comprises a first component that comprises a fibrinogen solution, and the prewet gelatin particles in the form of a wet paste also comprising an aqueous solution (approximately 150 mg/mL gelatin).

The Fibrinogen Solution

The concentration of fibrinogen in the formulations, kits and methods of the invention may be in the range between 15 and 150 mg/ml, between 40 and 100 mg/ml, or between 55 and 85 mg/ml.

In one kit, a component is composed of fibrinogen, and a co-stabilizer, such as arginine, lysine or 4-(aminomethyl)-cyclohexanecarboxylic acid (tranexamic acid), epsilon aminocaproic acid (EACA) and combinations thereof.

According to the invention, the components of the fibrin adhesive can be prepared from the initial blood composition. The blood composition may be whole blood or fractions of blood, that is, a whole blood product such as plasma. The fibrinogen component, proteolytic enzyme and catalyst can be autologous, human including the combined plasma, or of non-human origin.

In one embodiment of the invention, the fibrinogen component is composed of a biologically active component (BAC), which is a solution of proteins derived from blood plasma that may additionally comprise tranexamic acid and arginine or lysine or mixtures of arginine and lysine, or pharmaceutically acceptable salts thereof. The BAC can be derived from the cryoprecipitate, in particular from the concentrated cryoprecipitate. The term "cryoprecipitate" refers to a component of blood that is obtained from frozen plasma prepared from whole blood. A cryoprecipitate can be obtained when the frozen plasma is thawed cold, usually at a temperature of 0 to 4° C., which results in the formation of precipitated protein containing fibrinogen and Factor XIII The precipitate can be collected, for example, by centrifugation. The BAC solution further comprises Factor VIII, fibronectin, von Willebrand factor (vWF), vitronectin, etc., for example, as described in U.S. Pat. No. 6,121,232 and WO9833533. Preferably, the BAC composition may comprise stabilizers such as tranexamic acid and arginine hydrochloride. Generally, the amount of fibrinogen in the BAC is in the range between about 55 and about 85 mg/ml. The BAC solution is preferably free of tranexamic acid, or it can contain from about 0 to about 80 to about 110 mg/ml. The amount of arginine hydrochloride can be from about 15 to about 25 mg/ml.

Optionally, the solution is buffered to a compatible physiological pH value. The buffer may be composed of glycine, sodium citrate, sodium chloride, calcium chloride and water for injection as a vehicle. Glycine can be present in the composition in an amount between about 6 and about 10 mg/ml, sodium citrate can be in the range between about 1 and about 5 mg/ml, sodium chloride can be in the range between about 5 and about 9 mg/ml and the calcium chloride may be at a concentration of about 0.1 to 0.2 mg/ml.

In another embodiment, the concentration of plasminogen and plasmin in the BAC composition is reduced to be equal to or less than 15 µg/ml such as 5 µg/ml or less of plasminogen using a procedure as described in U.S. Pat. No. 7,125,569 and WO02095019.

It is also possible that the fibrin adhesive kit comprises components that stimulate clot formation, such as Ca2+, Factor VIII, fibronectin, vitronectin, von Willebrand factor (vWF) that can be provided as a separate component or formulated with the components of the fibrin adhesive.

The protein components of the fibrin adhesive can be prepared by recombinant procedures. It is also possible to prepare part of the protein components of the fibrin adhesive, or all of them, by recombinant procedures.

Fibrin adhesive components derived from blood compositions generally undergo viral inactivation processes to remove or minimize infectious particles. The viral inactivation processes can be carried out by nanofiltration, solvent/detergent treatment, heat treatment such as, but not limited to, pasteurization, gamma or UVC radiation (<280 nm), or by any other method known in the art. The term "infectious particle" refers to a microscopic particle, such as a microorganism or a prion, that can infect or spread in cells of a biological organism. Infectious particles can be viral particles.

The viral inactivation procedure can be carried out by adding a molecule to the composition or fraction of blood before and/or during the purification procedure. The added molecules and their products can be removed by gravitation, column chromatography or any other method known in the art.

The removal of infectious particles can be carried out by nanofiltration or by selective absorption procedures, such as hydrophobic, affinity and ion exchange chromatography. A viral inactivation procedure can be carried out in several stages. For example, the composition can be subjected to solvent/detergent treatment, heat treatment, selective chromatography and nanofiltration.

The Prewet Gelatin Particles

The prewet gelatin particles possess a higher degree of crosslinking and, therefore, swell to a lesser degree than the dry gelatin particles. The pre-wetting of these particles imparts optimal flowability for the resulting sealant. In addition, the prewet gelatin particles increase the viscosity and physically block the reacting components, lengthening the reaction process and imparting a longer working time for the end user.

The prewet gelatin particles typically originate from a porcine source, but may originate from other animal sources, such as from bovine or fish sources. The gelatin may be synthetically made, i.e., by recombinant means. The gelatin may be cross-linked. Any suitable cross-linking methods known to a person skilled on the art may be used including both chemical and physical cross-linking methods.

Preferably, the prewet gelatin is moistened in excess of ambiently absorbed moisture, such as 1 g of dry gelatin powder containing 1-10 g or water, saline, or other aqueous solution, more preferably 3-10 g of water/solution.

Suitable gelatin particles for use in or as the prewet gelatin particles are the gelatin particles of SURGIFLO® Hemostatic Matrix, commercially available from Ethicon Inc. Other commercially available gelatin materials useable in or as the swellable gelatin particles include Gelfoam (Pfizer), Curaspon (Cura Medical), Gelitaspon (Gelita Medical), and Gelaspon (KDM).

Second Component

The kit also comprises a second component comprising: (i) a thrombin solution, and (ii) dry gelatin particles.

The Thrombin Solution

The thrombin solution contains a proteolytic enzyme composed of thrombin. The thrombin solution generally comprises thrombin and calcium chloride. The initial activity of thrombin before the addition of the visualizing agent can be in the range between about 2 and about 4,000 IU/ml, or in the range between about 400 and about 1,200 IU/ml. The concentration of calcium chloride in the solution can be in the range between about 2 and about 6.2 mg/ml, or in the range between about 5.6 and about 6.2 mg/ml, such as at the concentration of 5.88 mg/ml. The thrombin solution may also comprise excipients. As used herein, the term "excipient" refers to an inert substance that is added to the pharmaceutical composition. Examples of excipients include, but are not limited to, human albumin, mannitol, sodium acetate and water for injection. The human albumin in the solution can be in the range between about 2 and about 8 mg/ml. Mannitol can be in the concentration range between about 15 and about 25 mg/ml. Sodium acetate can also be added to the solution in the range between about 2 and about 3 mg/ml.

The Dry Gelatin Particles

The dry gelatin particles in the second component possess a lower degree of crosslinking relative to the prewet gelatin particles of the first component and, therefore, provide a greater degree of swelling to the resulting sealant composition. However, the dry gelatin particles do not possess the desired flowability of the pre-wet gelatin particles within the first component.

The dry gelatin particles also typically originate from a porcine source, but may originate from other animal sources, such as from bovine or fish sources. The gelatin may be synthetically made, i.e., by recombinant means. The gelatin may be cross-linked. Any suitable cross-linking methods known to a person skilled on the art may be used including both chemical and physical cross-linking methods.

A suitable gelatin powder for use in or as the dry gelatin particles is SURGIFOAM® Absorbable Gelatin powder commercially available from Ethicon Inc. Other commercially available gelatin materials useable in or as the swellable gelatin powder include GELFOAM (Pfizer), CURASPON (Cura Medical), GELITASPON (Gelita Medical), and GELASPON (KDM) in powder or foam format.

Preparing and Using the Composition

The composition may be administered at the same time as, or itself comprise, one or more other biocompatible agents, such as those capable of stimulating hemostasis, wound healing, or tissue healing. This invention describes an in situ forming gelatin, fibrin sealant hydrogel/hydrocolloid composite sealant to be applied into lung tracts following a percutaneous or endobronchial biopsy procedure to prevent pneumothorax. The lung tract can have a varying diameter based on procedure, with a needle biopsy procedure ranging from 0.41 to 1.8 mm diameter to a novel coring procedure to remove a tumor nodule (<20 mm diameter). The sealant can polymerize within 30 s resulting in a biochemical seal and the composite sealant can swell upon hydration causing an additional mechanical seal to form. Additionally, the sealant could be utilized to seal any solid organ tracts including, but not limited to, liver, kidney, and spleen.

Examples of other agents include bioactive and non-bioactive agents including without limitation contrast agents such as iohexol, anti-infectives, such as antibiotics and antiviral agents; analgesics and analgesic combinations; anti-helmintics; antiarthritics; anticonvulsants; antidepressants; antihistamines; anti-inflammatory agents; antimigraine preparations; antineoplastics; anti-parkinsonism drugs; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; hormones, such as estradiol and other steroids, including corticosteroids; immunosuppressives; muscle relaxants; parasympatholytics; psychostimulants; naturally derived or genetically engineered proteins, polysaccharides, glycoproteins, or lipoproteins; oligonucleotides, antibodies, antigens, cholinergics, chemotherapeutic s, radioactive agents, radiopaque agents, osteoinductive agents, cystostatics heparin neutralizers.

The composition may be inserted into the lung tract either as a paste or as a dried plug. For example, the composition may be cast into a cylindrical mold with a diameter for example of less than 20 mm. It is then frozen, freeze dried, and released from the mold. The resultant plug is stiff and tough and can be utilized to seal lung needle biopsy tracts according to the invention.

Optionally, the mold may include features on its inside surface such that the resulting plug comprises for example lines, ribs, barbs, grooves, notches, slits, channels, spikes, steps, and combinations thereof. Or such features may be added to the finished plug by scoring, cutting, or other mechanical means.

The composition may be applied using an applicator as known in the art.

Optionally, the composition is held with a cylindrical mesh, moved into place, and the plug is deployed by expanding the mesh.

The following non-limiting examples further illustrate the invention.

In the Examples, "Gelatin I" means to refers to prewet gelatin particles in aqueous solution (e.g. SURGIFLO®) that meet the specifications defined by the United States Pharmacopeia (e.g., USP 29) and "Gelatin II" means to refers to dry gelatin particle powder (e.g. SURGIFOAM® powder) that meet the specifications defined by the United States Pharmacopeia (e.g., USP 29).

Example 1

A comparative kit was made as follows using the process shown in FIG. 1. The device is a Gelatin I-Gelatin II formulation that forms an interconnected network of fibrin that is further stabilized by endogenous fibrin. This embodiment contains one (1) unit of Gelatin I and one (1) unit of Gelatin II, five (5) mL of fibrinogen from an Evicel™ hemostatic kit, and five (5) mL of thrombin from an Evicel™ hemostatic kit. The resulting plug is a thick paste, can conforms well to the defect when applying a tamponade, and, once crosslinked is tough, elastic, and compressible.

Method of Making

To make an in-situ fibrin, gelatin composite sealant, fibrinogen can be first added to Gelatin II and is incorporated into the powder by vigorously shaking the powder container. Time should be provided to allow fibrinogen to physically interaction with the gelatin. The Gelatin II provides a scaffold for the fibrinogen to form, the ability of the sealant to swell, and increases the viscosity. The fibrinogen will form a monolayer surrounding the gelatin particles.

Thrombin should be added to Gelatin I as is currently done in the clinic. This can be generated using a dual syringe exchange method with at least six passes.

At the point of use, the fibrinogen-soaked powder can be rolled into a ball and transferred to a 20 mL syringe by hand. The Gelatin I-thrombin dispersion can be then mixed with the fibrinogen-soaked powder via the dual syringe exchange method with 10 passes. The sealant has a working time of approximately 30 seconds (Note: Typically, fibrin sealants have a working time of less than 5 seconds).

As depicted in FIG. 1, five (5) mL fibrinogen from an Evicel hemostatic kit is incorporated with one (1) unit of Gelatin II via vigorous shaking in Container 1. The Fibrinogen/Gelatin II mixture creates a ball of material. The plunger is removed from Syringe 1, the ball of material is transferred to Syringe 1, and the plunger is returned. Syringe 2 is filled with five (5) mL of thrombin from an Evicel hemostatic kit. Syringe 3 is filled with one (1) unit of Gelatin I. Syringe 2 and 3 are mixed via the dual syringe exchange method with 6 passes. Syringe 4 is filled with the mixture of thrombin and Gelatin I. Syringes 1 and 4 are mixed together to activate the sealant via the dual syringe method with 8 passes. The sealant has a 30 second working time.

A kit according to the invention was made as follows using the process shown in FIG. 2. The device is a Gelatin I-Gelatin II formulation that requires low expression force. This embodiment contains one (1) unit of Gelatin I, one (1) unit of Gelatin II, five (5) mL of fibrinogen from an Evicel hemostatic kit, and five (5) mL of thrombin from an Evicel hemostatic kit. The resulting plug is a thick paste, can conforms well to the defect when applying a tamponade, and, once crosslinked is tough, elastic, and compressible.

Method of Making

To make an in-situ fibrin sealant, gelatin composite sealant requiring lower expression force, thrombin should be first added to Gelatin II and is incorporated into the powder by vigorously shaking the powder container. The addition of thrombin (with a viscosity relative to fibrinogen) provides significantly reduces the viscosity of the Gelatin II-thrombin dispersion. Fibrinogen should be added to Gelatin I using a dual syringe exchange method with at least six passes. The fibrinogen will form a monolayer surrounding the gelatin molecules.

At the point of use, the thrombin-soaked powder can be rolled into a ball and transferred to a 20 mL syringe by hand. The Gelatin I-fibrinogen dispersion can be then mixed with the thrombin-soaked powder via the dual syringe exchange method with 10 passes. The sealant has a working time of approximately 30 seconds (Note: Typically, fibrin sealants have a working time of less than 5 seconds).

Figure 2:
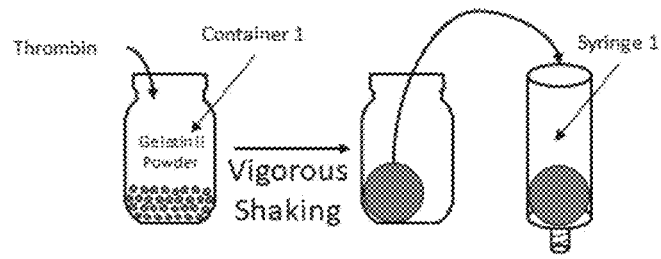
FIG. 2 is a diagram of the process used to make the kit according to the invention of Example 1.
Figure 2:
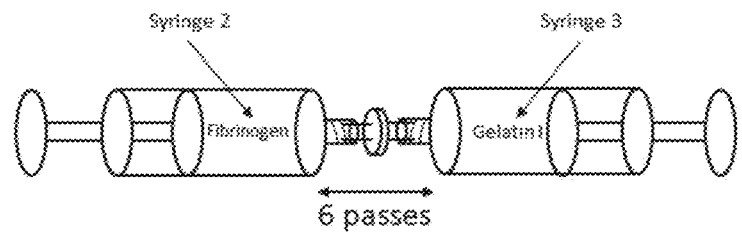
Figure 2:
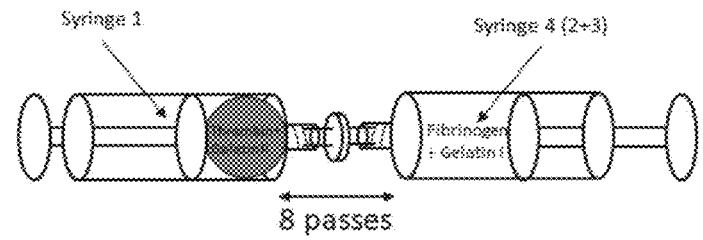
Figure 2:
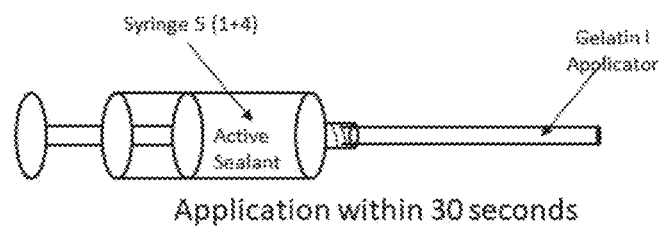

As depicted in FIG. 2, five (5) mL of thrombin from an Evicel hemostatic kits is incorporated with one (1) unit of Gelatin II via vigorous shaking in Container 1. The Thrombin/Gelatin II mixture creates a ball of material. The plunger is removed from Syringe 1, the ball of material is transferred to Syringe 1, and the plunger is returned. Syringe 2 is filled with 5 mL of fibrinogen from an Evicel hemostatic kits. Syringe 3 is filled with one (1) unit of Gelatin I. Syringe 2 and 3 are mixed via the dual syringe exchange method with 6 passes. Syringe 4 is filled with the mixture of fibrinogen and Gelatin I. Syringes 1 and 4 are mixed together to activate the sealant via the dual syringe method with 8 passes. The sealant has a 30 second working time.

Method of Sealing

The sealant can be applied using the typical Gelatin I applicator tip and crosslinks within 30 seconds. The viscosity and density of the sealant prevents the sealant from being disturbed by the positive pressure of the lung when on ventilation.

This embodiment results in a sealant that requires dramatically less expression force to mix using the dual syringe method than the second embodiment. The sealant has a similar flowability, consistency, and working time.

Example 2

Development of Gelatin/Biologics In Situ Sealants for Lung Tract Sealing

The purpose of this study was to assess different embodiments of combinations of gelatin (i.e. Gelatin I or Gelatin II) components with the biologic components of a fibrin sealant (i.e. Evicel).

Materials:
Gelatin I
Gelatin II
Evicel fibrin sealant (or hemostatic) kit, which consists of a vial of lyophilized fibrinogen (BAC2) and a vial of thrombin freeze dried powder, and reconstitution solutions and an application device

TABLE 1

| Syringe 1 | Syringe 2 | Fabrication Method | Expression force | Observations |
| --- | --- | --- | --- | --- |
| 1 unit Gelatin I + 1 unit Evicel Thrombin = 73 mg/mL gelatin, 403 IU/mL thrombin | 1 unit Gelatin I + 1 unit Evicel Fibrinogen = 73 mg/mL gelatin, 35 mg/mL fibrinogen | Dual Syringe Exchange 6 passes | + | Easy to generate sealant. Sealant was a thinner flowable. Good cohesiveness. Formulation has insufficient swelling |
| 1 unit Gelatin I + 1 unit Evicel Thrombin = 73 mg/mL gelatin, 403 IU/mL thrombin | 1 unit Gelatin II + 1 unit Evicel Fibrinogen = 200 mg/mL gelatin, 76 mg/mL fibrinogen | Dual Syringe Exchange 6 passes | ++++ | Fibrinogen was difficult to incorporate into Gelatin II. Very high expression force required to generate sealant. Sealant was a thick flowable sealant with a workable putty consistency. Good cohesiveness. More swelling observed. |

TABLE 1-continued

| Syringe 1 | Syringe 2 | Fabrication Method | Expression force | Observations |
|---|---|---|---|---|
| 1 unit Gelatin II + 1 unit Evicel Thrombin = 200 mg/mL gelatin, 887 IU/mL thrombin | 1 unit Gelatin I + 1 unit Evicel Fibrinogen = 73 mg/mL gelatin, 35 mg/mL fibrinogen | Dual Syringe Exchange 6 passes | ++ | Thrombin was easily incorporated in Gelatin II. Relatively low expression force required. Sealant was identical to previous sample. |

Note:
Gelatin II-Gelatin II formulations could not be tested as these formulations lacked any flowability.

The results are shown in Table 1. Conclusion: Addition of Gelatin II increased viscosity and swelling of gelatin/biologics formulations. The incorporation of thrombin into Gelatin II required a much lower expression force than incorporation of fibrinogen into Gelatin II.

Viscosity of Gelatin-Biologics Composite Sealants

The purpose of this study was to assess the viscosity of each component of gelatin-biologics sealants developed for lung tract sealing.

Materials:
Gelatin I
Gelatin II
Evicel Fibrin Sealant
Saline

Methods:
Viscosity measurements were taken on the following combinations shown in Table 2. In each combination, one (1) unit of biologic (5 mL) was combined with one (1) unit of gelatin.

TABLE 2

| Gelatin | Biologics | Concentrations |
|---|---|---|
| N/A | Fibrinogen | 76 mg/mL fibrinogen |
| N/A | Thrombin | 887 IU/mL thrombin |
| Gelatin I | Saline | 73 mg/mL gelatin |
| Gelatin I | Thrombin | 73 mg/mL gelatin, 403 IU/mL thrombin |
| Gelatin I | Fibrinogen | 73 mg/mL gelatin, 34 mg/mL fibrinogen |
| Gelatin II | Saline | 200 mg/mL gelatin |
| Gelatin II | Thrombin | 200 mg/mL gelatin, 887 IU/mL thrombin |
| Gelatin II | Fibrinogen | 200 mg/mL gelatin, 76 mg/mL fibrinogen |

Viscosity was measured via continuous rotational rheometry using a ThermoHaake Mars IQ Air. A 35 mm diameter parallel plate geometry held constant at 24° C. was utilized. 100-1000/s strain rates were tested in 10 linear steps. Note: Gelatin II and fibrinogen was unstable at strain rates >200/s and was therefore tested from 10-200/s. Viscosities were compared between formulations at 200/s.

Figure 3:
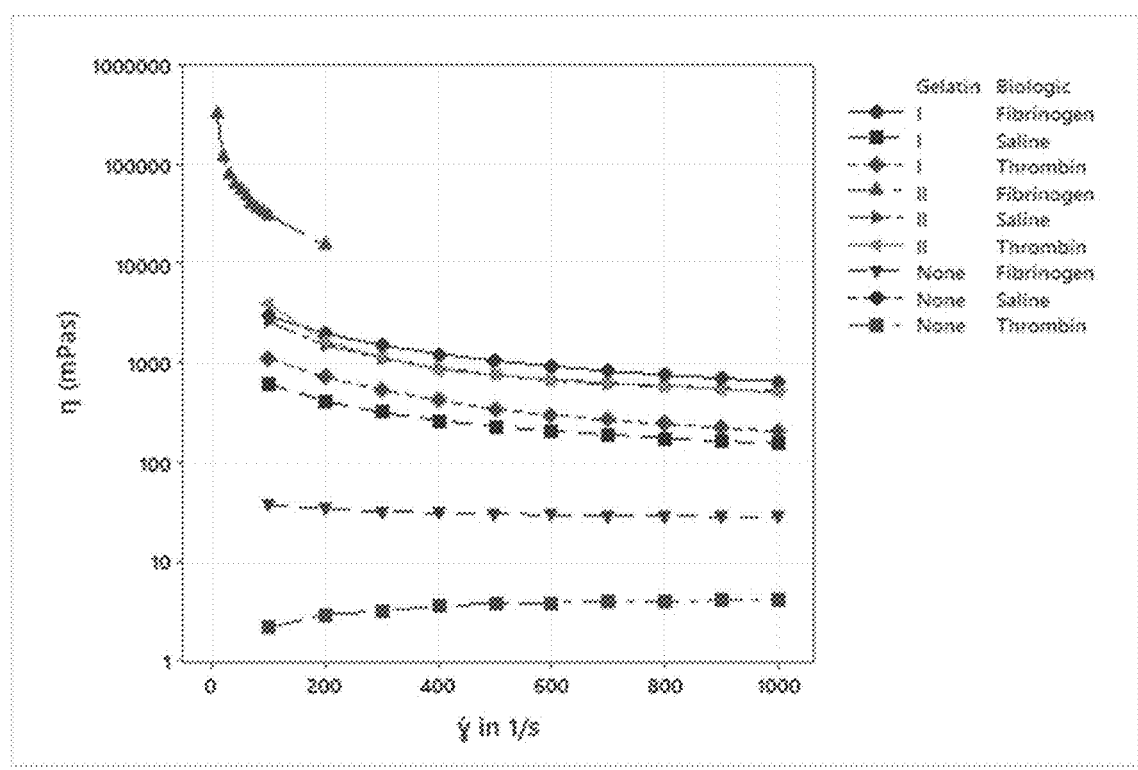
FIG. 3 is a graph showing the viscosity of compositions vs. strain rates for the results of Example 2.
Figure 4:
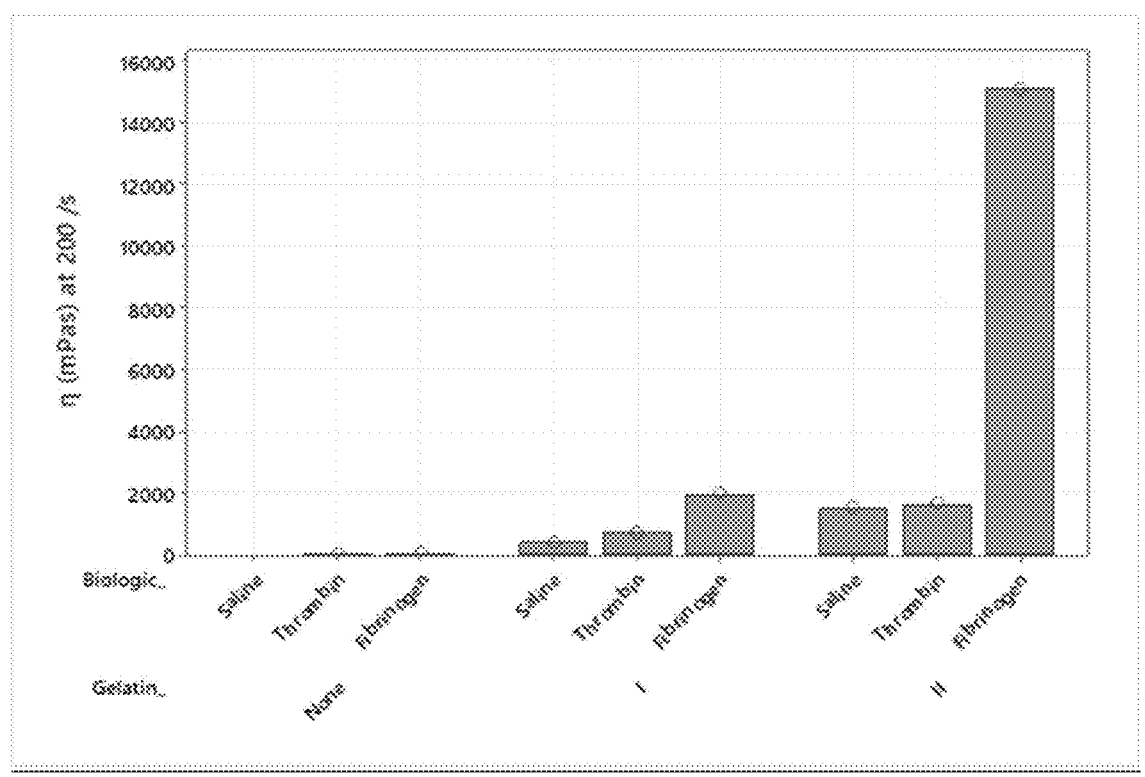
FIG. 4 is a bar graph showing the viscosity at the strain rate of 200/s of various compositions in Example 2.

The results are shown in FIGS. 3 and 4. Fibrinogen and thrombin exhibited Newtonian fluid properties. Gelatin based formulations demonstrated shear thinning properties. There was a significant effect caused by biologics ($p=0.003$, two-way ANOVA, Appendix) and gelatin ($p=0.002$, two-way ANOVA, Appendix).

Inclusion of gelatin, markedly increased viscosities by more than an order of magnitude. For Gelatin I-formulations, the inclusion of thrombin caused the viscosity to nearly double from 405 to 710 mPas. Inclusion of fibrinogen resulted in a nearly 5-fold increase 1950 mPas. For Gelatin II, this trend was further exacerbated with thrombin resulting in a slight increase of viscosity from 1498 to 1642 mPas. Incorporation of fibrinogen resulted in an increase of an order of magnitude to 15073 mPas. Gelatin II with fibrinogen could not be measured above 300/s because it was beyond its linear viscoelastic region and, therefore, unstable.

Discussion:

Gelatin I and Gelatin II with saline results in an increase of greater than 1 order of magnitude relative to the Evicel fibrin sealant alone. Gelatin I combined with saline, thrombin, and fibrinogen and Gelatin II combined with saline and thrombin result in comparable viscosities. However, when fibrinogen is combined with Gelatin II, the viscosity is increased by an order of magnitude relative to the other gelatin formulations.

Example 3

Ex-Vivo Results

Prototypes were evaluated for their ability to achieve pneumostasis in an ex vivo porcine large lung tract model. In this model, lung plucks were harvested fresh on the day of testing and kept moist until testing. Prior to testing, the lungs were placed on a ventilator to recruit collapsed alveoli (goal is to open up collapsed airless alveoli). At the time of testing, lungs were connected to a Respironics respirator to precisely control the pressure during ventilation cycles. The pressure was set to an inspiration pressure of 25 cm water and expiration pressure of 5 cm water ($\Delta$ 20 cm water).

Lung defects were created with a coring device with a diameter of 18 mm with resulting puncture size of approximately 20 mm diameter to depth of 3 cm. The air leak in the defect was assessed as severe with a bubble test. When prototypes were applied, pressure was reduced to inspiration pressure of 10 cm water and expiration pressure of 10 cm water (no change) to keep the lungs expanded.

After prototype application, typically topical compression was placed on prototype for 1 min while the lung was still expanded and under positive pressure. To test performance, lung was ventilated starting at low pressure and increasing to inspiration pressure of 25 cm water and expiration pressure of 5 cm water (Δ 20 cm water). Bubble test was performed by passing saline over puncture site and recording for presence and severity of air leak. For an additional challenge, ventilation pressures were increased to inspiration pressure of 40 cm water and expiration pressure of 5 cm water (Δ 35 cm water). After pressure testing, prototypes were pulled from puncture site and adherence to surrounding tissue was qualitatively assessed. The specific prototypes which were tested are listed in the caption for each image.

The results are shown in Table 3 in which L1-1 and L3-1 refer to the preferred embodiment in which the components of the sealant were prepared by mixing Gelatin I with fibrinogen and, separately, Gelatin II with thrombin. At the time of application, the two components were mixed and applied to the target tissue. L2-6 represents a control of fibrin sealant alone, which was not effective.

Figure 5:
FIG. 5 is a photograph of prototype L1-1 of Example 3.

FIG. 5 shows a photograph of prototype L1-1.

TABLE 3

| Prototype | Test Article | 20 cm H$_2$O Pressure | 35 cm H$_2$O Pressure | Adherence | Comments |
|---|---|---|---|---|---|
| L1-1 | Gelatin I/Gelatin II Evicel Fibrin Sealant | No Leaks | Small edge leak [1] | Adhered to surrounding tissue | Short working time; 3 min tamponade pressure; 4 cm depth (all others were 3 cm) |
| L2-6 | Evicel Fibrin Sealant | Leaked | Leaked | Minimal adherence | Applied 10 mL with Control tip |
| L3-1 | Gelatin I/Gelatin II Evicel Fibrin Sealant | Very small edge leak (resolved) | No Leak | Adhered well | Applied 15 mL Evicel/gelatin paste |

[1] Small leak created when seal was disturbed during premature adherence testing
[2] Small leak where tamponade pressure was applied
[3] Plug/Sealant disengaged on one edge and leaked at higher pressure The combination of components was mixed into a paste and injected directly into the defect created using a coring device. Topical compression was applied to the paste for 3 min while the lung was expanded and under positive pressure. No leaks were observed at 20 cm water. The sealant adhered well to the surrounding tissue. This same prototype was tested on a different lung (L3-1) during the same testing occasion and was also successful in sealing a defect created with a 20 mm biopsy punch.

We claim:

1. A kit for preparing a composition for sealing a tissue tract, comprising:
   a. a first component comprising: (i) a fibrinogen solution, and (ii) prewet gelatin particles in an aqueous solution; and
   b. a second component comprising: (i) a thrombin solution, and (ii) a dry gelatin powder;
   wherein the first and second components are stored separately and configured for mixing together to form a composition that is flowable and cross-linkable.

2. The kit of claim 1, wherein 90% of the prewet gelatin particles have a diameter of less than 1000 microns.

3. The kit of claim 1, wherein the prewet gelatin is moistened in excess of ambiently absorbed moisture.

4. The kit of claim 1, wherein the dry gelatin powder is in particle form wherein 90% the particles have a diameter of less than 2000 microns.

5. The kit of claim 1, wherein the aqueous solution is a saline solution.

6. A method of sealing a tissue tract, comprising:
   a) mixing
      (1) a first component comprising:
         (i) a fibrinogen solution, and
         (ii) prewet gelatin particles in an aqueous solution; and
      (2) a second component comprising:
         (i) a thrombin solution, and
         (ii) a dry gelatin powder;
   to form a flowable, rapidly cross-linkable composition at 37° C.; and
   b) injecting the composition into a tissue tract.

7. The method of claim 6, wherein the tissue is selected from the group consisting of lung tissue, kidney tissue, spleen tissue, liver tissue, and bone tissue.

* * * * *